(12) United States Patent
Reinhardt et al.

(10) Patent No.: US 7,627,959 B2
(45) Date of Patent: Dec. 8, 2009

(54) CENTRIFUGAL DRYER AND METHODS FOR THE CONTROL THEREOF

(75) Inventors: Jörg Reinhardt, Idstein (DE);
Burkhard Wandelt, Eschborn (DE);
Christoph Naumann, Konigstein (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 11/684,215

(22) Filed: Mar. 9, 2007

(65) Prior Publication Data

US 2007/0256319 A1 Nov. 8, 2007

Related U.S. Application Data

(63) Continuation of application No. PCT/EP2005/010367, filed on Sep. 24, 2005.

(30) Foreign Application Priority Data

Oct. 9, 2004 (DE) ........................ 10 2004 049 241

(51) Int. Cl.
*F26B 17/30* (2006.01)
(52) U.S. Cl. ............................................ 34/58; 34/528
(58) Field of Classification Search .................... 34/524, 34/528, 550, 58, 312, 482, 491; 219/707
See application file for complete search history.

(56) References Cited

U.S. PATENT DOCUMENTS

| 4,557,719 | A | | 12/1985 | Neumann et al. |
| 5,752,327 | A | * | 5/1998 | Biallas et al. .................. 34/359 |
| 6,624,386 | B2 | * | 9/2003 | Von Borstel ........... 219/121.84 |
| 2002/0118366 | A1 | | 8/2002 | Baldwin et al. |
| 2004/0057650 | A1 | * | 3/2004 | Folestad ....................... 385/14 |

FOREIGN PATENT DOCUMENTS

| DE | 4441350 | 6/1996 |
| DE | 19645923 | 5/1998 |
| DE | 10153353 | 5/2003 |
| JP | 11009897 A | * 1/1999 |

* cited by examiner

*Primary Examiner*—Jiping Lu
(74) *Attorney, Agent, or Firm*—Balaram Gupta

(57) ABSTRACT

A dryer for the removal of moisture or solvents from fine specialty chemicals and pharmaceuticals after their production, comprises a rotating drying compartment (2) which consists of at least one window (3), in operable relationship with an NIR probe (4) for measuring the moisture content of the product such as a specialty chemical or biological pharmaceutical contained in the closed drying compartment. The NIR probe (4) is positioned outside the drying compartment and is oriented through the at least one window (3) toward the product.

4 Claims, 1 Drawing Sheet

US 7,627,959 B2

CENTRIFUGAL DRYER AND METHODS FOR THE CONTROL THEREOF

CROSS-REFERENCE TO RELATED APPLICATIONS

Figure 1:
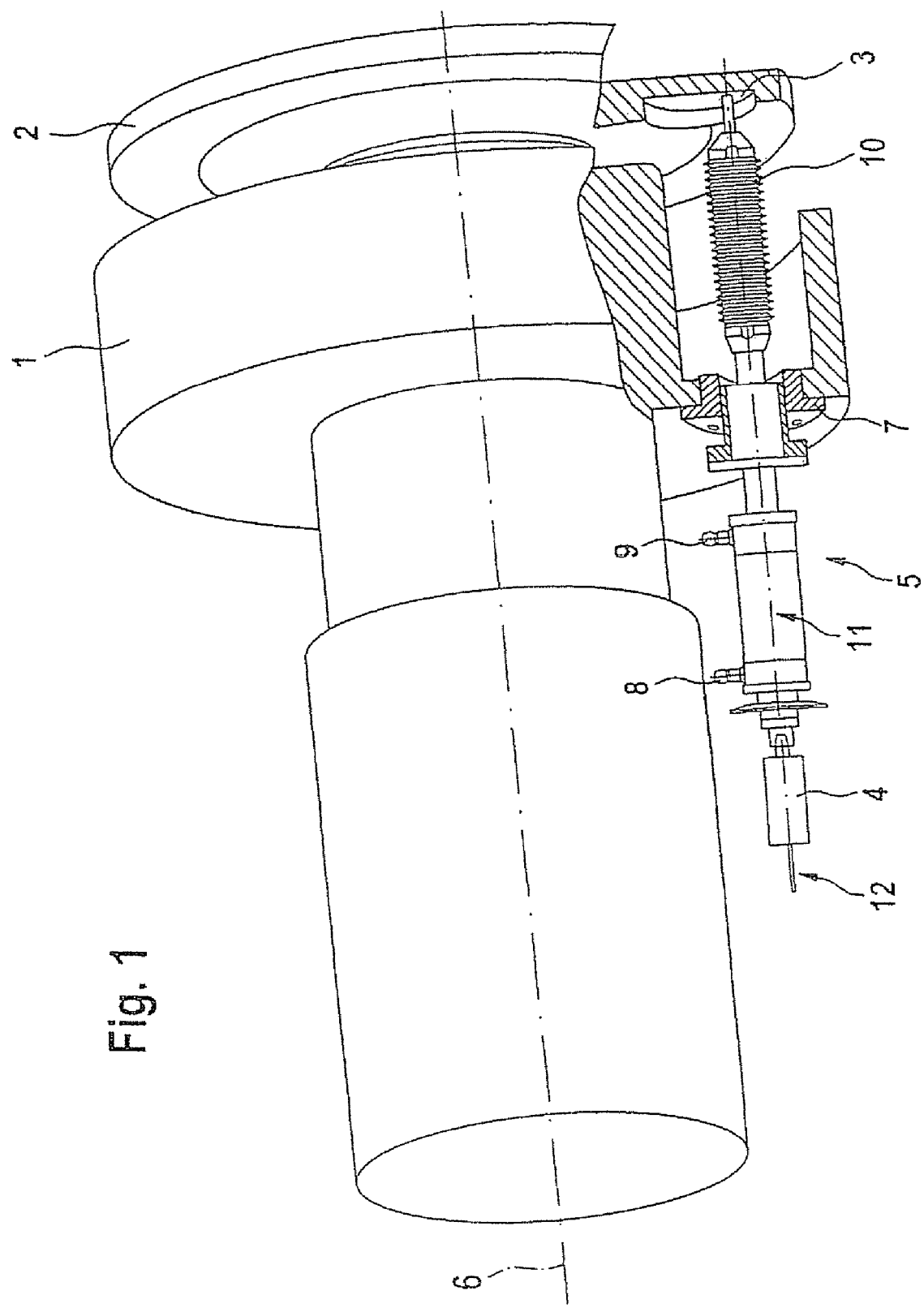

This application is a continuation of International Patent Application No. PCT/EP2005/010367 filed on Sep. 24, 2005 which is incorporated herein by reference in its' entirety which also claims the benefit of priority of German Patent Application No. 10 2004 049 241.7 filed on Oct. 9, 2004.

FIELD OF THE INVENTION

The invention relates to dryers and more particularly to centrifugal dryers to the removal of moisture and solvents from fine specialty chemicals and pharmaceuticals after their production. More specifically, the present invention relates to centrifugal dryers for the drying out and removal of moisture and solvents from highly labile and delicate pharmaceuticals such as biologicals and protein-containing compositions such as insulin and insulin-containing derivatives thereof. The centrifugal dryer of the present invention comprises a moving drying compartment for drying a product, in particular, an insulin-containing product, and to a method for controlling the dryers' operation further comprising an NIR probe for measuring the moisture of the product being dried.

BACKGROUND OF THE INVENTION

Centrifugal dryers and their use in the pharmaceutical and chemical industries are well known in the art. These dryers combine the two steps of centrifuging and drying into one apparatus. For example, in the isolation of pharmaceutical active substances, there are applications which require a combination of centrifugation at one time in a single unit and in which, by means of the centrifugal dryer, unintentional release during transport from the centrifuge to the dryer is avoided. Other applications thereof include the isolation of oxidation-sensitive or light-sensitive products as well as drying/moisture removal applications in aseptic processes.

U.S. Pat. No. 6,408,536 to Deusser et. al. discloses and claims a method for drying protein crystals starting from an aqueous protein crystal suspension in a centrifugal dryer. For example, insulin is used for the preparation of pharmaceutical formulations in crystalline form. For the stability of the crystal structure, insulin crystals require an optimum residual water content of from 2% to 10%. The drying process must therefore be appropriately and precisely stopped when this optimum residual water content range is reached.

The control of the drying process in the centrifugal dryer was achieved by known dryers of the prior art in two ways. First, a minimum drying time is established as a function of the loading of the dryer, and secondly, the drying process is stopped before the moisture in the $N_2$ drying exhaust gas falls below the 2.0% limit. For determining the actual residual moisture in the dried product, a sample of the product is then taken and the water content of the sample is determined by means of a Karl Fischer titration. However, the procedure in this method is relatively complicated despite the use of semi-automatic devices. The size of the sample quantity required for such a determination is within about a few hundred mg. The time required for a titration is typically from 5 to 20 minutes. The disadvantages of the prior art methods are that the samples have to be removed from the process whereby the method may detrimentally effect the chemical/pharmaceutical so dried and this also requires a substantial period of time. Moreover, particular chemicals that can be dried in this manner and a specific extraction are required and these can also be dried in the methods and dryers of the prior art.

Published U.S. Patent Appln. No. 2005000869 to Kessler et. al. discloses and claims a device for determining the residual liquid content of solid cakes in centrifuges, consisting of at least two sensors, in particular electrodes, and a measuring device connected to the sensors and intended for measuring the residual moisture, in particular a conductivity-measuring or capacitance-measuring device, the sensors being arranged a distance apart in the region of the centrifuge drum. However, this device has the disadvantage that there is direct contact between the product and the sensors so that deposits of the product on said sensors may occur. Mounting the sensors and measuring device on the rotating drum furthermore results in complicated arrangements for data transmission and for the voltage supply of the device, and corrosion protection precautions have to be taken.

DE A1 196 45 923 assigned to Bayer AG discloses another device for an on-line moisture measurement that is in contact with the product in a stationary (non-rotating) dryer. An optical measuring head for an on-line investigation of the moisture of agglomerated particles in dryers is used in, which measuring head consists of a pot-like sample chamber arranged vertically in the dryer and open at the top and an optical sensor which is closed in the sample chamber with a measuring window and produces an output signal characteristic of light diffusely reflected by the particle sample in the sample chamber. However, this measuring head is not rotatably moveable and is not suitable for a rotating centrifuge drum or centrifugal dryer.

Finally, U.S. Pat. Nos. 6,063,292 and 6,328,897 to Leung relates to a further method in which the surface cake moisture is measured in situ using an infrared reflection from a cake of solids within the drum of a drum centrifuge. A cake moisture monitoring means is arranged in the drum. A disadvantage of this method is once again the contact between product and cake moisture monitoring means. Furthermore, the surface moisture of the cake and not the average moisture content of the solids can be determined.

The object of the present invention avoids the disadvantages of the prior art and in particular, permits the on-line determination of the residual moisture of a material present in a dryer comprising a moving drying compartment, in a centrifugal dryer, without the need for contacting the product or removal thereof from the dryer.

SUMMARY OF THE INVENTION

The present invention relates to centrifugal dryers for the drying and removal of moisture and solvents from highly labile and delicate pharmaceuticals such as biological actives and protein-containing compositions such as insulin and insulin-containing derivatives thereof. The centrifugal dryer of the present invention comprises a moving drying compartment for drying a product, in particular, an insulin-containing product, and to a method for controlling the dryers' operation further comprising an NIR probe for measuring the moisture of the product being dried without contacting the product or interfering with the products' removal.

DETAILED DESCRIPTION OF THE DRAWING

FIG. 1 shows a section of a dryer of the present invention comprising a pneumatic fitting for the retention and positioning of the NIR probe.

DETAILED DESCRIPTION OF THE INVENTION

This object is achieved, according to the invention, by a dryer comprising a moving drying compartment, in particular a centrifugal dryer, the centrifuging and drying of a product, in particular an insulin-containing product. The dryer comprises a drying compartment mounted in a housing so as to be rotatable about an axis, in particular a centrifuge drum which can be closed by a restrictor plate. The drying compartment, in particular the restrictor plate of the centrifuge drum, contains at least one window. The dryer furthermore comprises an NIR probe for carrying out moisture measurement on the product in the closed drying compartment, the NIR probe being arranged outside the drying compartment and, in at least one position of the drying compartment, being oriented through the at least one window toward the product.

The dryer is preferably designed in such a way that the drying compartment, in particular the centrifuge drum, has a horizontally arranged axis and has a compact casing. The drum contains a cylindrical screen which is firmly connected to the drum. Different elements, such as Poroplate®, bar screens, filter cloths or special perforated metal plates, can be used for the screen. The filter fineness of the screen may be up to 1 μm. The space between the porous lateral surface of the screen and the compact lateral surface of the centrifuge drum is divided radially into a plurality of chambers. The rear end face of the centrifuge drum has openings, so that, during rotation of the centrifuge drum, either a gas (e.g. a drying gas) can be passed into the chambers from outside or a liquid (e.g. the mother liquor of a crystal suspension) can be drawn off from the chambers to the outside. The drying compartment is closed at the front by the restrictor plate which rotates with the drying compartment. When the drying compartment is at rest, the restrictor plate can be moved in the axial direction. When the restrictor plate is moved back, for example, a fixed circular outlet path which is then accessible from the interior of the drying compartment is opened. After the drying compartment has been opened, the drying compartment can rotate again slowly (in order to discharge the dry product). In the case of the dryer used for the present invention, however, other mechanisms known to the person skilled in the art are also possible for product discharge from the dryer, for example pushing the product out of the rotating drying compartment with the aid of a drum insert. The drying compartment is surrounded by a housing.

In the present invention, the diameter of the drying compartment, in particular of the centrifuge drum, is preferably from 200 mm to 1300 mm, and the casing length of the drying compartment is preferably from 100 mm to 600 mm.

The drying compartment, in a centrifuge dryer preferably the restrictor plate closing the centrifuge drum, contains at least one window in the dryer according to the invention. The window preferably has a thickness of from 10 mm to 20 mm and is advantageously produced from an infrared-transparent glass, e.g. borosilicate 3.3. It is particularly important that the window absorbs or reflects as small a proportion as possible of the radiation of the NIR probe.

In the present invention, the NIR probe is arranged outside the drying compartment and interacts with the product present in the drying compartment via the at least one window. The NIR probe serves for measuring the moisture of the product present in the drying compartment. The measurement is based on a spectroscopic method in which diffuse reflection of radiation in the near infrared (NIR) spectral range is determined. Such an NIR probe known in the prior art usually contains a measuring head comprising light-emitting and light-receiving optical fibers. Outside the measuring head, the light-receiving optical fibers are connected to the detector of a spectrometer and the light-emitting optical fibers are connected to a light source. Such an NIR probe is, for example, the Reflector fiber bundle probe from Solvias AG, Switzerland, which can be combined, for example, with a Matrix®-F spectrometer from Bruker Optik GmbH, Germany. A plurality of NIR probes of one dryer or different dryers can be connected simultaneously to the spectrometer. The light source and the detector of the spectrometer are then used jointly by the NIR probes. For example, the Matrix®-F from Bruker Optik GmbH has six channels for the connection of six fiber optic NIR probes. The evaluation of the spectra and the assignment of the spectra to an absolute residual product moisture content in percent are effected in the so-called chemometric model, which is deposited, for example, as a file on a computer belonging to the spectrometer. The moisture value determined there in percent is transmitted, for example via Profibus DP, to a process control system.

In the present invention, the NIR probe is oriented, in at least one position of the drying compartment, toward one of the windows or toward the window in the drying compartment so that the light emitted by the NIR probe illuminates the product present in the drying compartment through the window and light reflected by the product can be input through the window into the NIR probe. For carrying out a moisture measurement, the drying compartment is temporarily stopped in this position. For exact positioning of the drying compartment and hence of the window relative to the NIR probe which does not rotate concomitantly during the measurement, the dryer according to the invention, in particular the centrifuge dryer according to the invention, preferably contains a sensor for determining the angle of rotation of the drying compartment, in particular of the centrifuge drum.

In a particular embodiment of a centrifugal dryer, the window is in the region of the lower edge of the restrictor plate in the measuring position. This ensures that, even in the case of small amounts of product present in the drying compartment designed as a centrifuge drum, the window is at least partially covered from the inside by product in the measuring position so that it can be illuminated through the window with NIR radiation. For the same reasons, the NIR probe is preferably directed toward the lower part of the window in the measuring position. If necessary for optimum measurement owing to the properties of the NIR probe, the latter can also be oriented toward the window at a certain angle (e.g. 20°) relative to the horizontal.

The dryer according to the invention has the advantage that the moisture of the product can be directly measured during the drying process. This avoids contact between the product and the measuring apparatus by virtue of the fact that the NIR probe is arranged in front of the window outside the drying compartment, in particular in front of the window present in the restrictor plate of the centrifuge drum. The drying compartment and the screen thus remain free of internals, with the result that product deposits are prevented. Furthermore, there is no need to remove a sample of the product from the dryer for carrying out a moisture measurement, and moreover no sample preparation therefor is necessary.

According to a preferred embodiment of the present invention the NIR probe is less than 2 mm, preferably less than 1 mm, away from the window when a moisture measurement is carried out. By setting such a distance which is as small as possible, reliable measured results for the moisture of the product can be obtained.

According to another preferred embodiment of the dryer of the present invention, the NIR probe contains an optical system facing the drying compartment and a means for flushing the optical system with a gas being provided. Furthermore, the dryer according to the invention preferably comprises a device for flushing the at least one window with a gas. Thus, any product deposit forming on the optical system of the NIR probe and on the outside of the window can be eliminated since said deposit will influence the measured result. For example, during centrifuging of an insulin-containing product, a dust layer may form on the optical system of the NIR probe and on the outside of the window since fragments of insulin crystals which are smaller than the pores of the screen pass through the screen in the course of drying and may reach the outside of the restrictor plate from there. The means for flushing the optical system which are preferably provided according to the present invention and the device for flushing the window can, for example, blow the optical system and the window clear before each measurement by at least one gas pulse (in particular a nitrogen pulse). For this purpose, for example, a capillary for conducting the gas can be integrated into the optical system of the NIR probe.

According to a preferred embodiment of the dryer according to the invention, the NIR probe is held by a fitting in the housing surrounding the drying compartment. The fitting ensures retention of the NIR probe in a certain position and at a certain angle relative to the window in the restrictor plate. The fitting is mounted, for example, by making an opening in the housing, on which opening a special adapter flange which serves for fixing the fitting is attached.

According to a preferred embodiment of the present invention the restrictor plate is axially displaceable for opening and closing the drying compartment, and the NIR probe is held by a fitting connected to the housing, the fitting comprising pneumatic means for the axial displacement of the NIR probe. With this fitting, the NIR probe can likewise be axially displaced on axial displacement of the restrictor plate, e.g. for product discharge, so that the optical system of the NIR probe is not damaged by the displaced restrictor plate during opening of the drying compartment and so that, after the drying compartment has been closed, the NIR probe can be moved again sufficiently close to the restrictor plate and can be accurately positioned in order to be able to carry out reliable moisture measurements. The NIR probe is moved by the fitting, for example via a pneumatic drive.

By means of proximity switches belonging to the fitting, the end positions (measuring position and stand-by position) can be indicated. A bellows attached, for example, to the fitting permits movement of the NIR probe without danger of contamination.

The invention further relates to a method for controlling a dryer comprising a moving drying compartment, in particular a centrifugal dryer, which contains a drying compartment mounted in a housing so as to be rotatable about an axis and having at least one window, in particular a centrifuge drum, the method comprising the method steps of:

introduction of a product, in particular of an insulin-containing product, into the drying compartment, drying of the product, the closed drying compartment rotating, measurement of the residual moisture in the product using an NIR probe arranged outside the drying compartment through the window in the drying compartment and termination of the drying step when the measured residual moisture is less than the required residual moisture content.

The abovementioned statements regarding the dryer according to the invention also apply to the method according to the invention, where they are applicable.

For measuring the residual moisture using the NIR probe, the product is illuminated with NIR radiation through the window. A part of the radiation is absorbed by the water content in the product. In the light reflected back to the NIR probe by the product, the water-dependent part is attenuated. The light reflected back is guided by the NIR probe, for example by means of optical fibers, to NIR detectors whose signal is a measure of the residual moisture in the product.

The method according to the invention can be carried out, for example, with a protein-containing, in particular an insulin-containing, product. In the preparation of human insulin, an insulin crystal suspension is obtained by re-crystallization after a multiplicity of preparation and purification steps. This insulin crystal suspension is preferably transferred by means of nitrogen excess pressure from the crystallization container containing the suspension into the screen in a centrifuge drum of the centrifugal dryer according to the invention. In the centrifugal dryer, the crystals are then filtered off from the suspension. Thereafter, the insulin filter cake remaining in the screen after filtration is washed with water. The insulin filter cake is then dried in a plurality of drying steps in the centrifugal dryer. For example, the drying is initially effected by fixed-bed drying, after which the insulin filter-cake is blown off from the filter with the aid of a blow-off nozzle and then further dried by fluidized-bed drying. During the drying, according to the invention the residual moisture in the insulin to be dried is determined with the aid of the NIR probe at specified time intervals. The drying is complete when the insulin to be dried has reached a required residual moisture content, e.g. falls below a residual moisture content of, for example, 10%. The final insulin product can then be discharged from the centrifugal dryer. The method described here for human insulin can readily also be used in the drying of insulin analogs and insulin derivatives. In preferred embodiments, the present invention therefore relates to methods according to the invention for drying human insulin, insulin analogs and insulin derivatives.

In a preferred embodiment of the present invention, fixed-bed drying, fluidized-bed drying or a combination thereof is carried out in the dryer for drying the product. For fixed-bed drying, heated, compressed gas is used. Drying gas flows through the solid cake in the filter from inside to outside. As a result of the high flow rates achieved thereby, the liquid film on the surface of the solid particles is torn locally and the fine disperse droplets forming are removed through the filter to the outside with the gas flowing through. For carrying out further method steps subsequently, the filter-cake is blown off the filter wall by gas jet pulses. In fluidized-bed drying, the drying gas is passed to the back of the drum into the process compartment, flows around the filter cake and leaves the interior of the drum again through the filter, which now serves as a particle filter. This produces a fluidized bed which is constantly and thoroughly mixed by the slow rotation of the drum.

With a combination of the two drying methods, for example, first fixed-bed drying and then fluidized-bed drying are carried out. The measurement of the residual moisture according to the present invention can be effected while carrying out one or both drying methods, it being possible to determine the mean cake moisture during the fluidized-bed drying and the surface cake moisture during the fixed-bed drying.

According to a preferred embodiment of the present invention, the centrifuge drum, for measuring the residual moisture, is temporarily stopped in a certain position at defined time intervals, the position being determined by means of a measurement of the angle of rotation. The exact positioning of the centrifuge drum and hence of the window relative to the NIR probe during the moisture measurement is important for obtaining reliable measured results.

According to the preferred embodiment of the method according to the invention, after the end of the drying, for opening the centrifuge drum, a restrictor plate closing the centrifuge drum and the NIR probe are moved axially away from the centrifuge drum. The displacement of the NIR probe can be effected, for example, with the aid of a fitting described above.

Furthermore, the NIR probe and the window are preferably flushed with a gas before the measurement of the residual moisture of the product. The gas used for flushing is, for example, nitrogen, which is blown in pulses onto the window and the optical system of the NIR probe.

More specifically, in the preferred embodiment of the present invention the NIR probe is moved pneumatically to a distance of less than 2 mm, preferably <1 mm, from the window for measurement of the residual moisture. With the aid of a pneumatic fitting, the NIR probe can be moved in the housing and can be positioned with the necessary accuracy. The NIR probe is preferably moved toward the window and away from the window in a space which meets the requirements for aseptic methods. This is achieved in particular by surrounding the probe in the space within the housing in front of the window by a bellows so that no germs from the moving NIR probe can enter the space in which product discharge takes place when the restrictor plate is moved back. The space meets the requirements for aseptic methods if no germs are detectable by means of microbiological monitoring.

According to a further embodiment of the invention, the moist product which builds up in a ring on the filter surface is dried with the aid of compressed nitrogen regulated by a thermostat during this fixed-bed drying, flows through the filter-cake being from the inside to the outside here. If the filter-cake has built up in front of the inspection window to such an extent that the measuring position of the NIR probe is inside the insulin ring and hence representative measurement of the residual moisture in the cross section of the filter-cake is possible, and the measuring location is therefore always the same distance away from the filter surface, the residual moisture decreasing as a function of time can be measured at this representative point. This can be used for controlling the fixed-bed drying. The advantage is the achievement of the same residual moisture always, independently of treatment and product properties (e.g. crystal size) of the product to be dried, for example of a protein, such as insulin. The fixed-bed drying can therefore be terminated at the optimum time with regard to any further working-up steps, such as, for example, "purification" and/or fluidized-bed drying.

A further embodiment of the invention is the application of the procedure described in the previous paragraph to the removal of moisture from products in centrifuging processes. For carrying out the measurement, all that is necessary is to stop the centrifuge drum and to carry out the measurement through the inspection window. A probe which can be moved in the direction of the inspection window is furthermore required in order to be able to realize the small distance to the inspection window (<1 mm). Furthermore, using an apparatus according to the invention, it is possible to move the probe along the inspection window in the direction of the filter surface. This permits the recording of a moisture profile in the fixed bed at various distances from the filter surface. A quantitative determination of the total residual moisture in the material being dried is therefore possible.

Thus, a further embodiment of the invention is a method for controlling a dryer as described above, characterized in that the measuring position of the NIR probe (4) is at a representative point in the cross section of the filter-cake and hence always the same distance away from the filter surface, and the residual moisture decreasing as a function of time is measured at this representative point.

It will be appreciated that every suitable combination of the respective elements of the present invention may be interchanged with one or more of other similar, suitable components known in the art and changed in minor, non-functional respects. These additional embodiments of the invention are also regarded as failing within the scope of the claims herein. The examples detailed below are provided to better describe and more specifically set forth the elements and mechanics/operation of the present invention with reference to the drawing, but for obvious reasons cannot describe all of them. It is to be recognized that the examples therefore are for illustrative purposes only however, and should not be interpreted as limiting the spirit and scope of the invention as later recited by the claims that follow.

COMPARATIVE EXAMPLE 1

Table 1 below shows results of drying experiments which are based on a conventional method for termination of drying. The termination of drying was determined by the empirical formula drying time (h)=load (kg)·0.7.

The experiments were carried out using a centrifugal dryer unit TZT-s from FIMA with the following equipment features:
  sterile design
  fully automated
  cleaning in place (CIP)/sanitizing in place (SIP)
  drying gas transported in open loop
  explosion protection by ensuring an inert atmosphere in the drying compartment
  maximum excess pressure during operation=3 bar.

Before the final drying step in the fluidized-bed drying, the following process steps were carried out:
  transfer of an insulin crystal suspension by means of excess nitrogen pressure from the crystallization container to the drum filter surface of the centrifugal dryer
  washing of the insulin filter-cake
  passage of nitrogen through the insulin filter-cake during fixed-bed drying
  blowing off the insulin filter-cake with the aid of a blow-off nozzle
  beginning of the fluidized-bed drying time.

After the end of the drying and after filling, the residual moisture was determined in the laboratory with the aid of a sample (Karl Fischer titration). Table 1 below shows the results of 13 experimental runs with:

| Experiment | Load | Time | Moisture |
|---|---|---|---|
| 1 | 11984 | 554 | 4.1 |
| 2 | 15339 | 720 | 4.6 |
| 3 | 32686 | 2034 | 20.2 |
| 4 | 16172 | 736 | 5.4 |
| 5 | 16848 | 720 | 9.7 |
| 6 | 19536 | 860 | 2.5 |
| 7 | 19224 | 1160 | 13.6 |
| 8 | 20689 | 1020 | 1.9 |
| 9 | 27131 | 1138 | 6.5 |
| 10 | 29273 | 2358 | 7.4 |
| 11 | 27656 | 1302 | 7.8 |

-continued

| Experiment | Load | Time | Moisture |
|---|---|---|---|
| 12 | 26113 | 1448 | 4.1 |
| 13 | 26063 | 1380 | 11.6 | load = mass of insulin used, in g,
time = drying time in the fluidized bed in min and
moisture = water content of the end product measured after the end of drying (Karl Fischer titration), in % by mass.

The disadvantage of the conventional method is evident in the variation of the resulting end product moisture contents, which in some cases do not fulfill the specifications.

EXAMPLE

Table 2 below shows the results of the NIR moisture measurement in a centrifugal dryer according to the invention by the method according to the invention. Before the fluidized-bed drying, during which the residual moisture was determined by means of NIR measurement, the same process steps as in the comparative example with an insulin crystal suspension were carried out. This comprises (as in the comparative example) the same commercial centrifugal dryer, in which an NIR probe was introduced via a pneumatic interchangeable fitting into the centrifugal dryer housing and positioned there. The results from the 8 experimental runs with NIR moisture measurement are shown in table 2 below, with

| Experiment | Load | Time | KF moisture | NIR moisture |
|---|---|---|---|---|
| 1 | 9810 | 463 | 2.0 | 2.62 |
| 2 | 15737 | 764 | 3.9 | 3.97 |
| 3 | 11235 | 516 | 2.5 | 2.63 |
| 4 | 13464 | 636 | 3.3 | 3.16 |
| 5 | 15918 | 690 | 3.1 | 2.98 |
| 6 | 20608 | 957 | 2.6 | 2.62 |
| 7 | 21222 | 930 | 2.2 | 2.21 |
| 8 | 20973 | 864 | 3.1 | 2.90 | load = mass of insulin used, in g,
time = drying time in the fluidized bed in min,
KF moisture = water content of the end product measured after the end of drying (Karl Fischer titration), in % by mass and
NIR moisture = last inline moisture measurement (product still in the centrifugal dryer) by means of the NIR probe.

As is evident in table 2, the moisture measurement according to the invention via the method according to the invention using the centrifugal dryer according to the invention agrees very well with the moisture content of the end product according to Karl Fischer and permits termination of the fluidized-bed drying on reaching the desired moisture content of the end product.

FIG. 1 shows a section of a dryer according to the invention comprising a pneumatic fitting for retaining and positioning the NIR probe.

The section in FIG. 1 shows an assembly of a dryer according to the invention, reference numeral 1 designating a part of the housing which contains the restrictor plate 2 in the opened state. The restrictor plate 2 contains a window 3 toward which an NIR probe 4 is moved by a fitting 5. The restrictor plate 2 is rotatable about the symmetry axis 6 with the centrifuge drum (not shown) arranged to the right thereof in FIG. 1. The restrictor plate 2 and the centrifuge drum connected to it are present in FIG. 1 in the position in which the NIR probe 4 is oriented through the window 3 onto the product present in the centrifuge drum. The NIR probe 4 is displaceable axially (in the installation direction, e.g. along symmetry axis 6) with the aid of the fitting 5.

The fitting 5 comprises an adapter flange 7 with which the fitting 5 is fixed to the housing part 1. Furthermore, the fitting 5 comprises connections 8, 9 for the connection of hoses (not shown) which supply the pneumatic drive 11 with control air. The NIR probe 4 comprises a connection facility 12 for a hose (likewise not shown) for feeding a flushing gas (e.g. air or nitrogen), for flushing the optical system of the NIR probe 4 and the window 3 before a measurement is carried out. Furthermore, the fitting 5 comprises a bellows 10 which enables the NIR probe 4 to be moved toward and away from the window 3 under sterile conditions. The axial displacement of the NIR probe 4 is effected pneumatically.

LIST OF REFERENCE NUMERALS

1 Part of the housing
2 Restrictor plate
3 Window
4 NIR probe
5 Fitting
6 Symmetry axis
7 Adapter flange
8 First connection, control air (stand-by position)
9 Second connection, control air (measuring position)
10 Bellows
11 Pneumatic drive of the fitting
12 Connection for flushing line

What is claimed is:

1. An improved dryer for the removal of moisture or solvents from a product, comprising a rotating drying compartment consisting of a centrifugal drum, said improvement consisting of at least one window (3) and wherein the centrifugal drum is closeable by a restrictor plate (2) axially displaceable for opening and closing the drying compartment, in operable relationship with an NIR probe (4) for carrying out a moisture measurement of the product contained in the closed drying compartment, the NIR probe (4) located less than 2 mm outside the drying compartment held by a fitting (5) connected to a housing surrounding the restrictor plate (2), the fitting (5) comprising means for the axial displacement of the NIR probe (4) and further comprising an optical system oriented toward the product through the at least one window (3) and a means for flushing itself and the at least one window with a gas.

2. The dryer as recited in claim 1, wherein the product is a specialty chemical or pharmaceutical.

3. The dryer as recited in claim 2, wherein the product is a water-containing protein.

4. The dryer as recited in claim 3 wherein the product is insulin, an insulin analog or an insulin derivative.

* * * * *

UNITED STATES PATENT AND TRADEMARK OFFICE
CERTIFICATE OF CORRECTION

PATENT NO. : 7,627,959 B2  
APPLICATION NO. : 11/684215  
DATED : December 8, 2009  
INVENTOR(S) : Jorg Reinhardt et al.

Page 1 of 1

It is certified that error appears in the above-identified patent and that said Letters Patent is hereby corrected as shown below:

In column 8, line 11, delete "failing" and insert -- falling --, therefor.

In column 9, line 28, delete "with" and insert -- with: --, therefor.

In column 10, line 57, in Claim 4, delete "claim 3" and insert -- claim 3, --, therefor.

Signed and Sealed this
Fourteenth Day of June, 2011

David J. Kappos
*Director of the United States Patent and Trademark Office*